United States Patent [19]
Bondinell et al.

[11] 4,192,888
[45] * Mar. 11, 1980

[54] PHARMACEUTICAL COMPOSITIONS AND METHOD OF INHIBITING PHENYLETHANOLAMINE N-METHYLTRANSFERASE

[75] Inventors: William E. Bondinell, Cherry Hill, N.J.; Robert G. Pendleton, Philadelphia, Pa.

[73] Assignee: SmithKline Corporation, Philadelphia, Pa.

[*] Notice: The portion of the term of this patent subsequent to Dec. 5, 1995, has been disclaimed.

[21] Appl. No.: 894,664

[22] Filed: Apr. 10, 1978

[51] Int. Cl.² .................... A61K 31/18; A61K 31/135
[52] U.S. Cl. ...................................... 424/321; 424/330
[58] Field of Search ............................... 424/321, 330; 260/556 B, 578

[56] References Cited

U.S. PATENT DOCUMENTS

| | | | |
|---|---|---|---|
| 3,060,091 | 10/1962 | Witkin | 260/578 |
| 3,505,404 | 4/1970 | Peterson et al. | 424/330 X |
| 3,835,188 | 9/1974 | Weyer et al. | 424/322 X |
| 4,128,666 | 12/1978 | Bondinell et al. | 424/330 |

*Primary Examiner*—Albert T. Meyers
*Assistant Examiner*—H. Steven Seifert
*Attorney, Agent, or Firm*—Joseph A. Marlino; Richard D. Foggio; William H. Edgerton

[57] ABSTRACT

Pharmaceutical compositions and methods of inhibiting phenylethanolamine N-methyltransferase using 2-indanamine compounds having 4 and/or 5 substituents.

5 Claims, No Drawings

PHARMACEUTICAL COMPOSITIONS AND METHOD OF INHIBITING PHENYLETHANOLAMINE N-METHYLTRANSFERASE

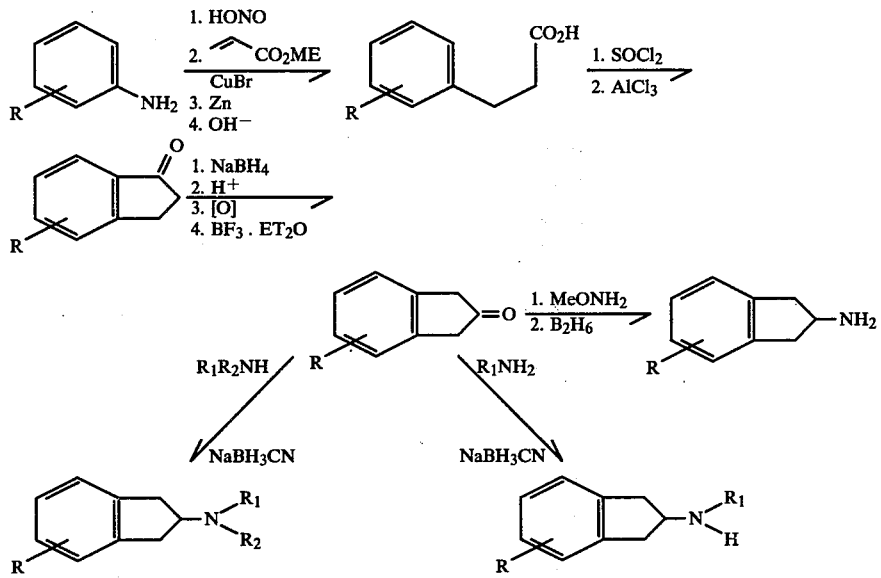

This invention relates to new pharmaceutical compositions and methods of inhibiting phenylethanolamine N-methyltransferase with 2-indanamine compounds having 4 and/or 5 substituents.

Epinephrine is a hormone, synthesized in the adrenal medulla, which is released into the blood stream in response to stress and produces profound physiological changes which serve to prepare the animal to cope with the stressor situation. For example, epinephrine produces anxiety, an increase in blood pressure, acceleration of heart rate and increase in cardiac output. These changes are detrimental in individuals with certain disease conditions such as angina pectoris, myocardial infarction and anxiety neuroses.

Phenylethanolamine N-methyltransferase catalyzes the final step in the biosynthesis of epinephrine, that is the transfer of a methyl group from S-adenosylmethionine to norepinephrine to produce epinephrine.

The 2-indanamine compounds of the pharmaceutical compositions and methods of this invention inhibit phenylethanolamine N-methyltransferase and thus reduce the formation of epinephrine. They are therefore useful in situations where there is overproduction of epinephrine or where epinephrine production is detrimental.

The compounds which are the active ingredients of the pharmaceutical compositions and methods of this invention are represented by the following formula:

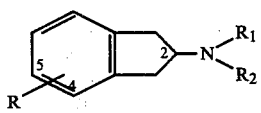

FORMULA 1

R is chloro, bromo, fluoro, iodo, trifluoromethyl, nitro, sulfamyl or methylthio with R being in either the 4 or 5 position; and $R_1$ and $R_2$ are hydrogen, methyl or ethyl; and pharmaceutically acceptable acid addition salts thereof.

The compounds of this invention are prepared by the following procedure:

The terms R, $R_1$ and $R_2$ are as defined above.

According to the above procedure, the 2-indanamines are prepared by reacting a substituted aniline with nitrous acid, methyl acrylate and cuprous bromide to form the corresponding substituted phenylpropionic acid. The acid is cyclized to the 1-indanone which in turn is converted to the 2-indanone and reduced to the desired 2-indanamine. The cyclization is carried out by treating the phenylpropionic acid with thionyl chloride and aluminum chloride or other Friedel-Craft catalysts.

An alternative method of preparing the phenylpropionic acid may be carried out by brominating a 2,3 substituted toluene and alkylating the resultant compound with diethyl malonate. The cyclization of the phenylpropionic acid may also be carried out with an acid catalyst such as polyphosphoric acid.

Pharmaceutically acceptable, acid addition salts of the compounds of Formula 1 are formed with organic and inorganic acids by methods known to the art. The base is reacted with an organic or inorganic acid in aqueous miscible solvent, such as acetone or ethanol, with isolation of the salt by concentration and cooling or in aqueous immiscible solvent, such as ethyl ether or chloroform, with the desired salt separating directly. Exemplary of the salts which are included in this invention are maleate, fumarate, benzoate, ascorbate, pamoate, succinate, bismethylenesalicylate, methanesulfonate, ethanedisulfonate, benzenesulfonate, acetate, propionate, tartrate, salicylate, citrate, gluconate, lactate, malate, mandelate, cinnamate, citraconate, aspartate, stearate, palmitate, itaconate, glycolate, p-aminobenzoate, glutamate, theophylline acetates, hydrochloride, hydrobromide, sulfate, cyclohexylsulfamate, phosphate and nitrate salts.

2-Indanamines and 2-aminohalo substituted indanes are generally known in the art. The latter compounds are disclosed in German Patent No. 1,518,652 as analgetics and vasodilators.

The basic activity of the compounds of this invention is demonstrated by inhibition of phenylethanolamine N-methyltransferase in vitro by the assay procedure described by Pendleton and Snow, Molecular Pharmacology, 9-718-725, 1973, at various compound concentrations. For example, following are in vitro results obtained from testing several compounds present in the pharmaceutical compositions and methods of this invention.

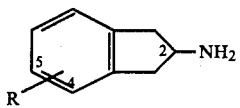

| SK&F No. | R | In Vitro Inhibition % $10^{-4}$ | $10^{-6 M}$ |
|---|---|---|---|
| 85391 | 5-NO$_2$ | 96 | 23 |
| 85506 | 5-Cl | 96 | 37 |
| 85347 | 5-Br | 96 | 33 |

In addition, the activity of the compounds of this invention is demonstrated in vivo by oral administration to rats at 50 mg./kg. three times over a 24 hour period. One hour after the last dose the rats are given a tracer dose of $^3$H-norepinephrine into a tail vein. Forty-five minutes later they are sacrificed by decapitation and the adrenals assayed for $^3$H-epinephrine and $^3$H-norepinephrine. A compound is considered active as a PNMT inhibitor if it significantly (at least $p<0.05$) decreases the conversion of radioactive norepinephrine into epinephrine (R. G. Pendleton et al., J. Pharmacol. Exp. Ther., 190:551-562, 1974, and R. G. Pendleton et al., J. Pharmacol. Exp. Ther., 197:623-632, 1976). A preferred compound of this invention, 5-sulfamoyl-2-aminoindane, significantly inhibited this conversion ($p<0.01$) at a unit dose of 50 mg./kg.

The pharmaceutical compositions of this invention to inhibit phenylethanolamine N-methyltransferase comprise a pharmaceutical carrier and, as the active ingredient, a 2-indanamine compound of Formula 1. The active ingredient will be present in the compositions of this invention in an effective amount to inhibit phenylethanolamine N-methyltransferase.

Preferably, the compositions of this invention contain the active ingredient of Formula 1 in an amount of from about 50 mg. to about 1000 mg., advantageously from about 100 mg. to about 500 mg., per dosage unit.

The pharmaceutical carrier may be for example a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 gm. Exemplary of liquid carriers are syrup, peanut oil, olive oil, sesame oil, propylene glycol, polyethylene glycol (mol. wt. 200-400) and water. The carrier or diluent may include a time delay material well known to the art such as, for example, glyceryl monostearate or glyceryl distearate along or with a wax.

A wide variety of pharmaceutical forms can be employed, for example, the preparation may take the form of tablets, capsules, powders, troches, lozenges, syrups, emulsions, sterile injectable liquids or liquid suspensions or solutions.

The pharmaceutical compositions are prepared by conventional techniques involving procedures such as mixing, granulating and compressing or dissolving the ingredients as appropriate to the desired preparation.

The method of inhibiting phenylethanolamine N-methyltransferase, according to this invention, comprises administering to an animal in an amount sufficient to inhibit phenylethanolamine N-methyltransferase a 2-indanamine compound of Formula 1.

Preferably the compounds of Formula 1 are administered in conventional dosage unit forms prepared by combining an appropriate dose of the compound with standard pharmaceutical carriers.

Preferably the active ingredient of Formula 1 will be administered in a daily dosage regimen of from about 100 mg. to about 2000 mg., most preferably from about 200 mg. to about 1000 mg. Advantageously, equal doses will be administered preferably two to three times per day. When the administration is carried out as described above, inhibition of phenylethanolamine N-methyltransferase is produced.

The route of administration of the pharmaceutical compositions of this invention and in accordance with the methods of this invention is internal, either parenteral or preferably oral, in an amount to produce the desired biological activity.

The following examples are not limiting but are illustrative of this invention.

EXAMPLE 1

6.35 g. of 2-chloroaniline (0.05 mole) in acetone (100 ml.) and concentrated hydrobromic acid (16 ml.) was stirred at $-5°$ C. and treated with a solution of 4.2 g. of sodium nitrite (0.06 mole) in water (10 ml.). Methyl acrylate (0.5 mole) (43 g.) and cuprous bromide (100 mg.) were then added at 0° C. The reaction temperature was kept below 15° C. until nitrogen evolution ceased and then stirred at 25° C. for thirty minutes. The reaction mixture was poured into water and extracted with benzene which was dried over sodium sulfate and evaporated to give methyl 2-bromo-3-(2-chlorophenyl)propionate.

The propionate, 138 g. (0.5 mole) was dissolved in glacial acetic acid (1 l.) and stirred. Zinc dust 65 g. (1 mole) was added in portions and the mixture was stirred for one hour, filtered and evaporated to give methyl 3-(2-chlorophenyl)propionate.

Methyl 3-(2-chlorophenyl)propionate was refluxed in 10% aqueous sodium hydroxide (1 l.) for two hours and the reaction mixture was cooled, acidified and filtered. The filter cake was dissolved in hot aqueous sodium bicarbonate and filtered. The filtrate was acidified and filtered to yield 3-(2-chlorophenyl)propionic acid.

The propionic acid 2.0 g. (0.011 mole) was suspended in benzene (27 ml.) and treated with 1.7 g. of thionyl chloride (0.014 mole) and dimethyl formamide (two drops). The reaction was refluxed for thirty minutes, filtered and evaporated to give 3-(2-chlorophenyl)propionyl chloride which was dissolved in chlorobenzene (12 ml.) and treated with anhydrous aluminum chloride 2.4 g. (18 mmoles). The reaction was stirred for one hour and poured onto ice. The chlorobenzene was evaporated in vacuo and the residue was extracted with chloroform which was washed, dried over sodium sulfate and evaporated to give 4-chloro-1-indanone.

The above prepared indanone 1.66 g. (0.01 mole) was dissolved in ethanol (30 ml.) and treated with 0.5 g. of sodium borohydride (0.013 mole). The reaction was stirred at 25° C. for one hour and evaporated. Ether was added to the residue followed by 10% hydrochloric acid. The ether was dried and evaporated to yield 4-chloro-1-indanol.

1.68 g. of the indanol (0.01 mole) and a trace of p-toluene-sulfonic acid in benzene (30 ml.) was refluxed for four hours. The benzene solution was evaporated to give 4-chloro-1-indene and 4-chloro-2-indene.

7.5 g. of the above mixture of indenes (0.05 mole) in chloroform (125 ml.) was treated with 10.0 g. of m-chloroperbenzoic acid (0.05 mole) at 5° C. The solution was allowed to warm to 25° C. and was stirred for sixteen hours. The chloroform was evaporated and the residue was dissolved in carbon tetrachloride which was extracted with aqueous sodium bicarbonate, dried and evaporated to give a mixture of 4-chloro-1,2-epoxyindane and 4-chloro-2,3-epoxyindane.

The mixture of above epoxyindanes was dissolved in ether (100 ml.) and cooled. Boron trifluoride etherate (100 ml.) was added below 15° C. and the reaction was stirred for thirty minutes. Water was added slowly and the ether layer was separated, washed with aqueous sodium bicarbonate, dried over sodium sulfate and evaporated. The residue was chromatographed on silica gel eluted with benzene to give 4-chloro-2-indanone.

4-Chloro-2-indanone 3.3 g. (0.02 mole) and 4.2 g. of methoxyamine hydrochloride (0.05 mole) were dissolved in a mixture of ethanol (42 ml.) and pyridine (42 ml.) and heated on a steam bath for thirty minutes. The reaction was diluted with water and the O-methyl oxime of 4-chloro-2-indanone was isolated by filtration.

0.78 g. of the O-methyl oxime of 4-chloro-2-indanone (4 mmoles) dissolved in tetrahydrofuran (5 ml.) was treated with 1 M diborane in tetrahydrofuran (20 ml.) and refluxed for two hours in an argon atmosphere. Methanol was added and the solvent was evaporated. The residue was treated with 10% hydrochloric acid and heated on a steam bath for thirty minutes. The mixture was made alkaline and extracted with ether which was dried over potassium carbonate and evaporated to yield 4-chloro-2-indanamine.

EXAMPLE 2

Following the procedure of Example 1, the following substituted aniline compounds:

2-bromoaniline
2-fluoroaniline
2-iodoaniline
2-nitroaniline
2-trifluoromethylaniline are used as starting materials to give the following products respectively:
4-bromo-2-indanamine
4-fluoro-2-indanamine
4-iodo-2-indanamine
4-nitro-2-indanamine
4-trifluoromethyl-2-indanamine

EXAMPLE 3

1.75 g. of N-acetyl-2-indanamine (0.01 mole) was added to 20 g. of chlorosulfonic acid (0.18 mole), stirred at −60° C. and allowed to warm to 25° C. The mixture was stirred until the reaction was complete, poured into cold water and extracted with ethyl acetate. Evaporation gave the crude N-acetyl-5-chlorosulfonyl-2-indanamine which was converted to N-acetyl-5-sulfamyl-2-indanamine with ammonia in THF. The N-acetyl sulfonamide was purified by recrystallization from water, m.p. 237°–239° C. and hydrolyzed in refluxing 10% hydrochloric acid to give 5-sulfamyl-2-indanamine which was recrystallized from methanol-ether, m.p. 261°–264° C.

EXAMPLE 4

5.6 g. of N-acetyl-5-chlorosulfonyl-2-indanamine (0.02 mole) (as prepared in Example 3) is dissolved in acetic acid (50 ml.), warmed to 75° C., and 19 g. of stannous chloride (0.1 mole) in concentrated hydrochloric acid (20 ml.) is added. An exotherm occurs. When the reduction is complete the mixture is cooled to 25° C. and poured into water. The N-acetyl-5-mercapto-2-indanamine is filtered and suspended in methanol (50 ml.) under a nitrogen atmosphere. 5.7 g. of methyl iodide (0.04 mole) and 1.1 g. of sodium methoxide (0.02 mole) are added and the mixture is stirred for one hour. The mixture is filtered, evaporated and the residue purified by chromatography to give N-acetyl-5-methylthio-2-indanamine which is hydrolyzed following the procedure of Example 3 to give 5-methylthio-2-indanamine.

EXAMPLE 5

A mixture of 0.4 g. of 5-chloro-2-indanone (0.0025 mole) was partially dissolved in methanol (10 ml.) and 0.4 g. of sodium cyanoborohydride (0.0065 mole) and 0.6 g. of dimethylamine hydrochloride (0.0075 mole) were added. The pH of the mixture was adjusted to 4.5 with 10% hydrochloric acid and 3 A molecular sieves were added. The mixture was stirred for 16 hours at 25° C., acidified, evaporated to dryness, dissolved in 10% hydrochloric acid, extracted with ether, basified and extracted with ether to yield N,N-dimethyl-5-chloro-2-aminoindane.

EXAMPLE 6

Following the procedure of Example 5, 5-chloro-2-indanone and methylamine hydrochloride gave N-methyl-5-chloro-2-indanamine.

EXAMPLE 7

| Ingredients | Mg./Capsule |
|---|---|
| 5-Chloro-2-indanamine | 150 mg. |
| Lactose | 150 mg. |

The above ingredients are mixed and filled into a hard gelatin capsule.

EXAMPLE 8

| Ingredients | Mg./Tablet |
|---|---|
| 5-Sulfamyl-2-indanamine | 50 |
| Calcium sulfate dihydrate | 150 |
| Sucrose | 25 |
| Starch | 15 |
| Talc | 5 |
| Stearic Acid | 3 |

The sucrose, calcium sulfate and indanamine are thoroughly mixed and granulated with hot 10% gelatin solution. The wetted mass is passed through a No. 6 mesh screen directly onto drying trays. The granules are dried at 120° C. and passed through a No. 20 mesh screen, mixed with starch, talc and stearic acid and compressed into tablets.

Two tablets are administered three times a day.

EXAMPLE 9

25 g. of 2-indanamine hydrochloride (0.15 mole), 20 g. of sodium acetate trihydrate (0.14 mole), and 40 g. of acetic anhydride (0.4 mole) were stirred at 25° C. for sixteen hours. The mixture was evaporated and the residue was partitioned between chloroform and water. The chloroform extracts were pooled, washed with 10% hydrochloric acid and then with 5% aqueous sodium carbonate, dried and evaporated to yield N-acetyl-2-indanamine.

18.5 g. of the acetamide (0.105 mole) was added in portions to nitric acid (185 ml.; d=1.51), stirred and maintained below 0° C. The reaction was allowed to warm to 0° C., poured onto crushed ice and extracted with chloroform which was washed with 5% aqueous sodium bicarbonate and evaporated to give crude N-acetyl-5-nitro-2-indanamine which was purified by crystallization from isopropanol, m.p. 143°–144° C.

12.6 g. of N-acetyl-5-nitro-2-indanamine (0.057 mole) in ethanol (200 ml.) containing 0.5 g. of 10% palladium-on-carbon catalyst was treated with hydrogen until the theoretical amount of hydrogen was absorbed. The catalyst was filtered and the filtrate was treated with concentrated hydrochloric acid (5 ml.) and evaporated. The residue was recrystallized from ethanol to give N-acetyl-5-amino-2-indanamine hydrochloride, m.p. 259°–260° C. (dec.)

4.0 g. of N-acetyl-5-amino-2-indanamine hydrochloride (0.018 mole) stirred below 10° C. in concentrated hydrochloric acid (6 ml.) and water (15 ml.) was treated with a solution of 1.5 g. of sodium nitrite (0.022 mole) dissolved in water (5 ml.). The resulting solution of diazonium salt was added to a stirred mixture of 2 g. of cuprous chloride (0.021 mole) in concentrated hydrochloric acid (6 ml.) and water (10 ml.) which was then stirred for 90 minutes and allowed to warm to 25° C.

The resulting mixture was extracted with chloroform which was washed, dried and evaporated. The residue was dissolved in ethyl acetate-cyclohexane (3:2) and chromatographed on neutral alumina to give N-acetyl-5-chloro-2-indanamine which was recrystallized from carbon tetrachloride and then from carbon tetrachloride-petroleum ether, m.p. 117°–119° C.

The acetamide, 1 g. (0.005 mole) was stirred and refluxed in 3 N HCl (10 ml.) for 3.5 hours and the mixture was evaporated. The residue was recrystallized from ethanol-ether and then from ethanol to give 5-chloro-2-indanamine hydrochloride, m.p. 273° C. (dec.)

EXAMPLE 10

N-Acetyl-5-nitro-2-indanamine, 1.5 g. (0.007 mole) as prepared in Example 9 was refluxed in 10% hydrochloric acid for 3 hours. The mixture was evaporated and the crystalline residue recrystallized from methanol-ether to yield 5-nitro-2-indanamine hydrochloride, dec.>280° C.

EXAMPLE 11

Following the procedure of Example 9, 2.85 g. of N-acetyl-5-indanamine (0.015 mole) in 48% hydrobromic acid (4 ml.) and water (10 ml.) was diazotized with 1.1 g. of sodium nitrite (0.016 mole) in water and added to 2.2 g. of cuprous bromide in 48% hydrobromic acid (4 ml.) and water (5 ml.) to give N-acetyl-5-bromo-2-indanamine which was recrystallized from chloroform-petroleum ether, m.p. 103°–105° C.

The N-acetyl compound was hydrolyzed with 3 N hydrochloric acid and purified by recrystallization from ethanol to give 5-bromo-2-indanamine, m.p. 280°–281° C. (dec.)

What is claimed is:

1. A method of inhibiting phenylethanolamine N-methyltransferase which comprises administering to an animal requiring said treatment an amount sufficient to produce said inhibition of a chemical compound of the formula:

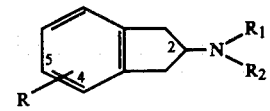

in which:
R is chloro, bromo, fluoro, iodo, trifluoromethyl, nitro, sulfamyl or methylthio with R being in either the 4 or 5 position; and
$R_1$ and $R_2$ are hydrogen, methyl or ethyl.

2. The method of claim 1 in which R is chloro.

3. The method of claim 2 in which R is 5-chloro and $R_1$ and $R_2$ are hydrogen.

4. The method of claim 1 in which R is 5-sulfamyl and $R_1$ and $R_2$ are hydrogen.

5. The method of claim 1 in which the compound is administered in a daily dose of from about 100 mg. to about 2000 mg.

* * * * *